(12) United States Patent
Belle et al.

(10) Patent No.: US 10,485,489 B1
(45) Date of Patent: Nov. 26, 2019

(54) SYSTEM AND METHOD FOR ASSESSING AND MONITORING THE HEMODYNAMIC CONDITION OF A PATIENT

(71) Applicant: Fifth Eye Inc., Ann Arbor, MI (US)

(72) Inventors: Ashwin Belle, Ann Arbor, MI (US); Bryce Benson, Ann Arbor, MI (US); Mark Salamango, Ann Arbor, MI (US)

(73) Assignee: Fifth Eye Inc., Ann Arbor, MI (US)

( * ) Notice: Subject to any disclaimer, the term of this patent is extended or adjusted under 35 U.S.C. 154(b) by 0 days.

(21) Appl. No.: 16/216,807

(22) Filed: Dec. 11, 2018

(51) Int. Cl.
| | |
|---|---|
| *A61B 5/04* | (2006.01) |
| *A61B 5/00* | (2006.01) |
| *A61B 5/0456* | (2006.01) |
| *A61B 5/024* | (2006.01) |
| *A61B 5/044* | (2006.01) |
| *A61B 5/0472* | (2006.01) |
| *A61B 5/0245* | (2006.01) |

(52) U.S. Cl.
CPC .......... *A61B 5/746* (2013.01); *A61B 5/0245* (2013.01); *A61B 5/02405* (2013.01); *A61B 5/044* (2013.01); *A61B 5/0456* (2013.01); *A61B 5/0472* (2013.01); *A61B 5/726* (2013.01)

(58) Field of Classification Search
CPC ..... A61B 5/746; A61B 5/0245; A61B 5/0472; A61B 5/0456; A61B 5/726; A61B 5/02405; A61B 5/44
See application file for complete search history.

(56) References Cited

U.S. PATENT DOCUMENTS

2019/0030331 A1* 1/2019 Ghosh .................. A61N 1/3603

* cited by examiner

*Primary Examiner* — Mallika D Fairchild
(74) *Attorney, Agent, or Firm* — Jeffrey Schox; Caitlin Ploch

(57) ABSTRACT

A system for assessing and monitoring the hemodynamic condition of a patient includes a signal processor and optionally a premise processing system. Additionally, the system can include a biosignal detection device, memory, a display, and any other suitable component. A method for assessing and monitoring the hemodynamic condition of a patient includes: receiving input data; determining a set of windows based on the input data; preprocessing each of the set of windows; processing each of the set of windows; determining a set of features for each of the set of windows; determining a hemodynamic condition for each window based on the set of features; and presenting the hemodynamic condition to a user.

20 Claims, 9 Drawing Sheets

US 10,485,489 B1

SYSTEM AND METHOD FOR ASSESSING AND MONITORING THE HEMODYNAMIC CONDITION OF A PATIENT

TECHNICAL FIELD

This invention relates generally to the biosignals field, and more specifically to a new and useful system and method for assessing and monitoring hemodynamic stability in the biosignals field.

BACKGROUND

For patients experiencing adverse events during a hospital stay, intervention often comes too late, which can result in any or all of: extended hospital stays, high readmission rates, unexpected crashes, reactive/crisis-response medicine, worse outcomes, higher costs, and hard-to-review patient cases. This is a significant problem in the healthcare industry, as approximately one third of patients experience adverse events during their hospital stays. Some causes of sudden patient deterioration include, for instance: bleeding (e.g., undetected bleeding, hemorrhage, etc.), sepsis, heart failure, pneumonia, trauma, a brain condition (e.g., traumatic brain injury, stroke, etc.), respiratory failure, hemodynamic decomposition, cardiogenic shock, cardiac arrest, pain, arrhythmias, infection, level of consciousness, and combinations of these.

Eighty-five percent of severe adverse events are preceded, however, by abnormal, underlying physiological signs; being able to respond to these early warning signs reduces mortality by seventy-five percent and associated costs by forty-percent. Current practices for monitoring patient health (spot-checked vital signs, physical exams, and lab tests) and the metrics involved (e.g., arterial blood pressure, heart rate, arterial hemoglobin oxygen saturation, etc.) do not enable such early detection. First, these practices involve inconsistent, incorrect, and infrequent measurements, as well as intermittent and blind gaps between measurements. Second, taking/recording these measurements is a manual process and requires action from a healthcare provider, such as nurse. Third, and perhaps most limiting, is that the human body has impressive compensatory systems, which often shield these underlying physiological signs from current methods of detection, resulting in late intervention. Real-world physiologic signal quality and morphology can be affected by a host of factors, including but not limited to: comorbidities (e.g., arrhythmia heart defects), background noise, lead placement, patient movement, medications (e.g., beta blockers, vasopressors), palliative care patients (e.g., highly medicated patients will have stable vital signs due to high levels of sedation/stabilizing drugs; patient physiology is highly altered and does not resemble that of deteriorating patients), other interventions (e.g., fluids, ventilator, etc.), or other factors.

Thus, there is a need in the biosignals field to create a new and useful system and method for detecting patient instabilities sooner and more reliably (given real-world data).

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
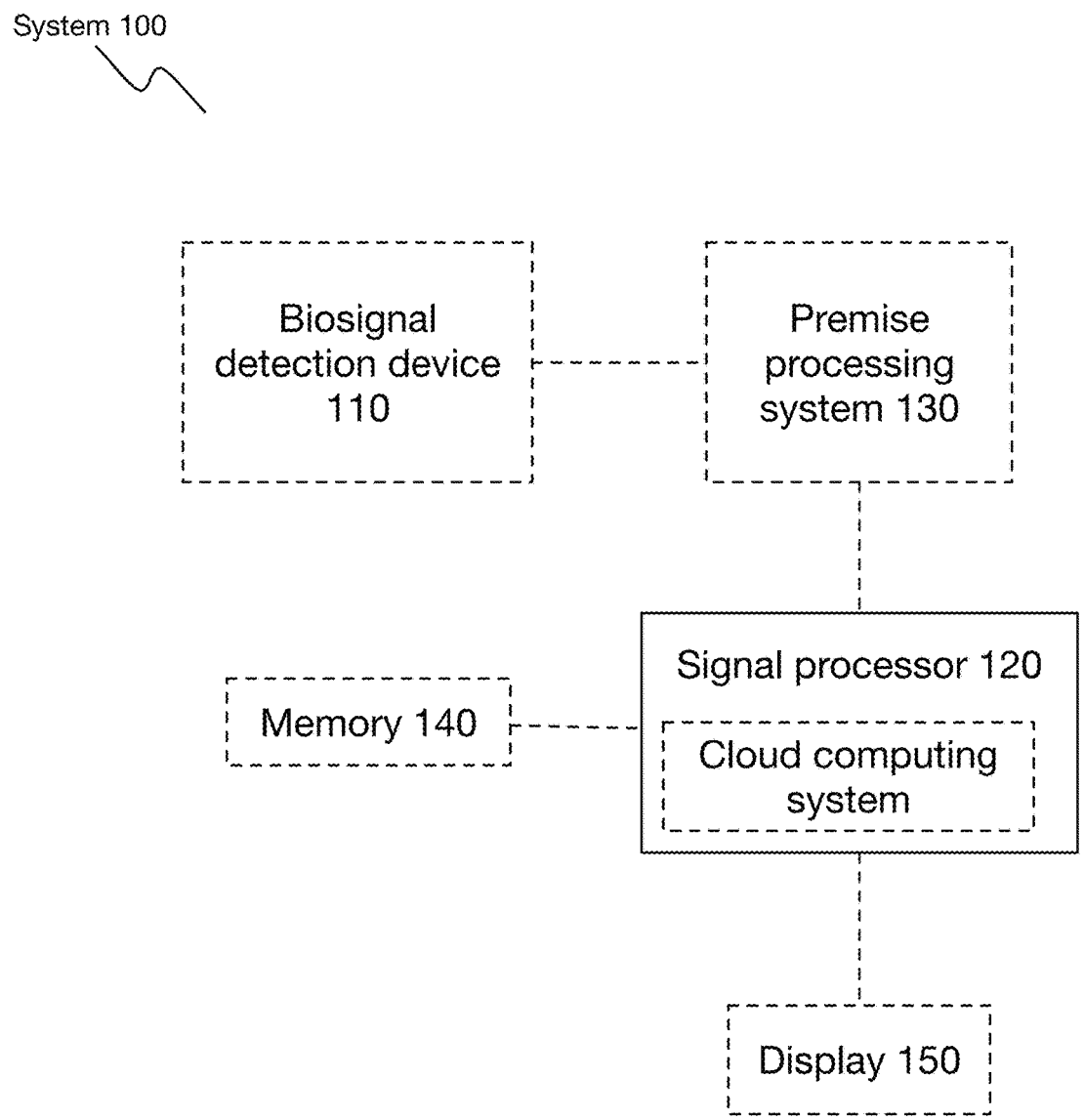
FIG. 1 is a schematic representation of the system.

As shown in FIG. 1, a system 100 for assessing and monitoring the hemodynamic condition of a patient includes a signal processor 120. Additionally, the system 100 can include any or all of: a premise processing system 130, biosignal detection device 110, memory 140 (equivalently referred to as storage), a display 150, and any other suitable component.

Figure 2:
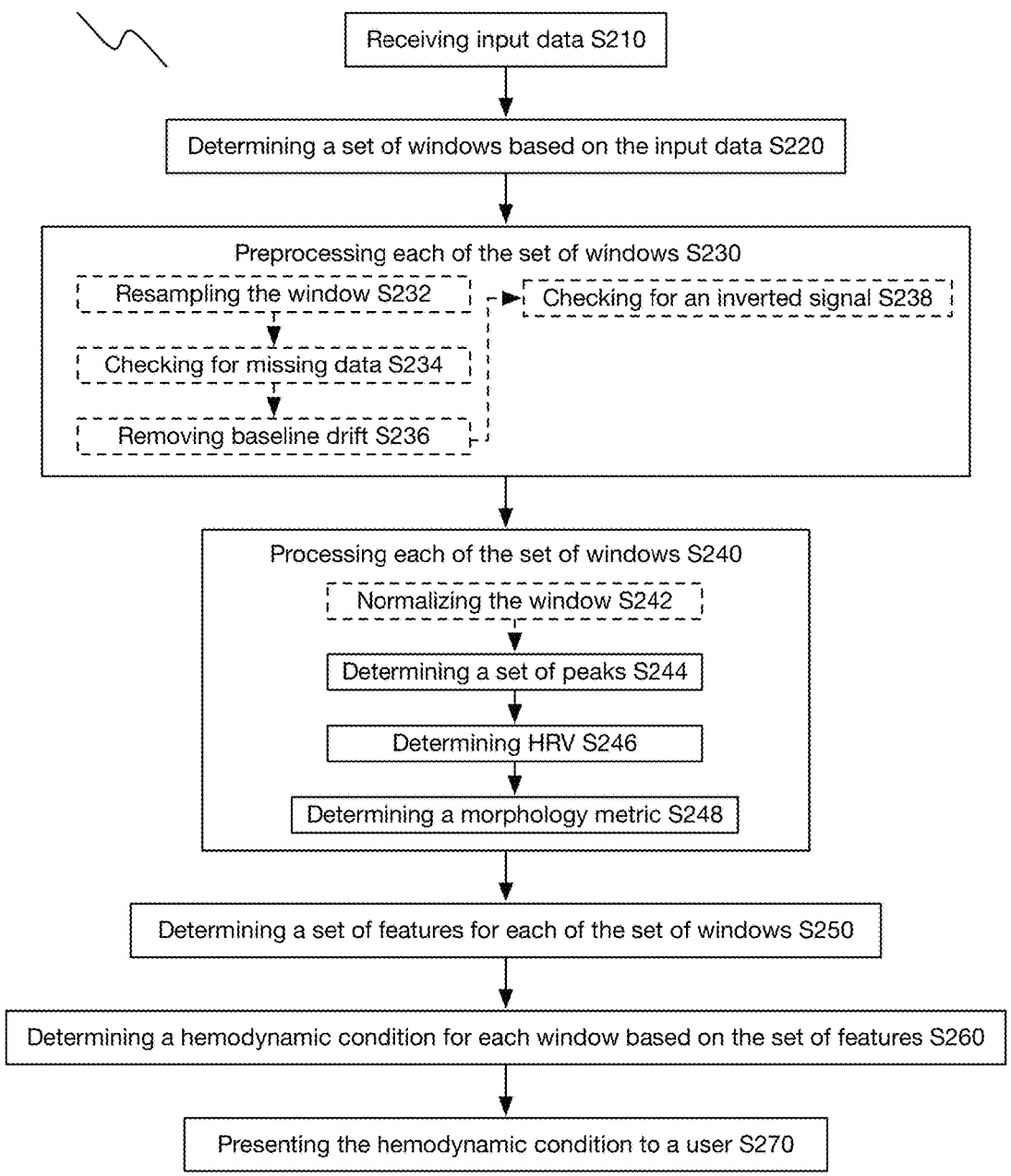
FIG. 2 is a schematic representation of the method.

As shown in FIG. 2, a method 200 for assessing and monitoring the hemodynamic condition of a patient includes: receiving input data S210; determining a set of windows based on the input data S220; preprocessing each of the set of windows S230; processing each of the set of windows S240; determining a set of features for each of the set of windows S250; determining a hemodynamic condition for each window based on the set of features S260; and presenting the hemodynamic condition to a user S270.

2. Benefits.

The system and method can confer several benefits over existing systems and methods for monitoring the health of a patient and successfully intervening if necessary.

First, the system and method can confer the benefit of providing a metric for effectively monitoring (e.g., high frequency monitoring, automatic monitoring, etc.) hemodynamic stability, which serves as a direct indicator of autonomic nervous system burden and an early predictor of sudden patient deterioration. In some variations, the system and method prevent sudden and serious patient deterioration by enabling prediction of future deterioration much sooner than existing systems and methods.

Second, the system and method can confer the benefit of providing an indication of hemodynamic stability in a short period of time (e.g., in substantially real time with the recording of the patient's electrocardiogram [ECG] signal) and/or with minimal starting information (e.g., a small dataset for the given patient). In some variations, a first indication of hemodynamic condition can be determined in five minutes without any baseline signal or measurement required.

Third, the system and method can confer the benefit of determining a metric for hemodynamic instability with a single or otherwise minimal amount of information, such as information already being recorded in an emergency setting. In some variations, for instance, only a single existing ECG waveform is needed to determine the metric.

Fourth, the system and method can confer the benefit of automatically providing a frequently-updated assessment of a patient's health. This can function to provide, for instance, near-real-time feedback (e.g., advance warning) on the success or safety of a treatment option. In some variations, for instance, feedback that a newly-administered drug is working can be quickly determined.

Fifth, the system and method can confer the benefit of providing easy-to-interpret historical trends (e.g., for a single patient, for multiple patients, etc.) without the need for electronic health record (EHR) inputs. In one example, different patient hemodynamic conditions and/or data classes can be visually represented by graphics having different size and color (e.g., tall red bars for at risk (e.g., unstable conditions), short green bars for stable conditions, black bars for missing data, gray bars for noisy data, etc.).

Sixth, the system and method can confer the benefit of reducing a median lead time before intervention, such as a call to a rapid response team. In some variations, for instance, the median lead time before a call to a rapid response team is significantly reduced (e.g., less than half of the time, less than a quarter of the time, etc.). In a specific example, use of the system and/or method results in an identification of patient deterioration more than 7 hours (e.g., 7.7 hours, less than 7.7 hours, greater than 7.7 hours, between 7-9 hours, between 5-20 hours, etc.) before a call to a rapid response team would be made.

Seventh, the system and method can confer the benefit of producing a minimal number of false positives and/or false negatives. In some variations, the method results in a 95% specificity or greater.

Eighth, the system and method can confer the benefit of reducing the length of stay of a patient in a healthcare facility, as well as a reduce the number of patient readmissions.

Ninth, the system and method can confer the benefit of assessing a patient's health independently of the patient's heart rate.

Tenth, the system and method can confer the benefit of enabling the processing of complicated real-world data (e.g., coming from sick patients) in a meaningful way through any or all of: removing complicated noise, removing baseline drift, managing (e.g., identifying, interpolating, etc.) missing data, managing unexpected signal morphologies, or any other process. In some variations, an improved signal quality index (e.g., that accommodates background noise, missing data, unexpected signal morphologies, or other effects on the signal) is used to enable the processing of complicated data. The system and method can further confer the benefit of enabling the processing of data from a variety of patients with the same processing workflow (e.g., both sick and healthy patients, both patients having noisy data and patients having clean data, etc.).

Eleventh, the system and method can confer the benefit of being personalized to each patient (e.g., through patient-specific features to track individual signal morphology changes over the course of monitoring), which can account for any or all of: detecting changes in patient health, detecting a patient response to treatment, or any other suitable event.

Additionally or alternatively, the system and method can confer any other suitable benefit(s).

3. System.

As shown in FIG. 1, the system 100 includes a signal processor 120 and optionally a premise processing system 130 (e.g., premise server, virtual machine, etc.). Additionally, the system 100 can include any or all of: a biosignal detection device 110, memory 140 (equivalently referred to as storage), a display 150, and/or any other suitable component.

The system 100 functions to receive a set of inputs including physiological data (e.g., one or more biosignals) determined from a user (e.g., sampled from a user) and process set of inputs to determine a metric for assessing and monitoring the patient's condition.

Inputs to the system include one or more biosignals, preferably including at least an electrocardiogram (ECG) signal stream (equivalently referred to as an ECG waveform), but can additionally or alternatively include any of the following biosignals: a pulse oximetry waveform produced from photoplethysmography (PPG), an arterial blood pressure (ABP) waveform, an intracranial waveform, an electroencephalogram (EEG) signal waveform, and any other suitable biosignal. The biosignals are preferably continuously monitored and recorded by the system 100, but can alternatively be sent in batches or other otherwise received at the system 100. Inputs can optionally include: patient kinematic data (e.g., sampled by an accelerometer attached to the patient's bed, sampled by a user device, etc.), patient treatment data, ambient environment data (e.g., sampled by ambient environment sensors in the patient's room), or any other suitable data.

Additionally, the set of inputs can further include any or all of: patient information (e.g., demographic information, health history, etc.), healthcare facility information, information associated with a biosignal detection device (e.g., signal type, device identifier), patient morbidity or medical condition, or any other suitable information.

The system 100 functions to classify a patient hemodynamic condition (e.g., stable condition, at risk condition, etc.) and to produce a continuous, temporal record of this condition. The temporal record can additionally include a classification of data quality of the incoming inputs (e.g., noisy data, missing data, etc.).

In one variation, an output of the system is a visual graphic with different visual rendering parameters associated with different output parameters. In an example, for instance, a temporal record of hemodynamic condition is displayed as a bar graph, with time as the y-axis. The bar height and color are correlated with the patient's hemodynamic classification (e.g., "stable" is associated with a short green bar, while "at risk" is associated with a tall red bar). The bar width preferably spans the sampling window, and is left-aligned at the sampling window's first timestamp. In another variation, the hemodynamic condition values for one or more patients can be presented as one or more trend lines. In another variation, the hemodynamic condition can be visualized as a deviation from a baseline, wherein the baseline can be associated with a stable condition (e.g., for the patient, for a general population, for the biosignal detection device, etc.). However, the data can be otherwise visualized.

The system 100 is configured to interface with, and can optionally include, a biosignal detection device 110, which is configured to measure one or more biosignals of a patient. In preferred variations, the biosignal detection device 110 is configured to measure an ECG signal (e.g., from an ECG monitor). Additionally or alternatively, the biosignal detection device 110 can be configured to measure any suitable biosignal or set of biosignals, each of which can be equivalently referred to as a physiologic signal.

The system includes a signal processor 120, which functions to process the set of one or more biosignals (e.g., ECG waveform data) and optionally any other inputs to produce a set of features from which a metric (e.g., value, classification, score, etc.) for patient condition (e.g., metric for hemodynamic instability) is ultimately determined. The signal processor 120 can execute the set of processes involved in the method 200 described below, or any other suitable set of processes.

The signal processor can optionally include a cloud computing system (e.g., cloud-based analytics engine), which functions to execute all or a portion of the processing. Additionally or alternatively, the signal processor can include a local (e.g., on-premise) computing system, a premise processing system (e.g., premise computing system, processing system operating on a biosignal detection device 110, virtual machine, etc.), or any other suitable computing system.

In one variation, the system receives de-identified ECG waveform data at a cloud computing system (e.g., remote computing system) and produces a classification or score characterizing the patient condition (e.g., hemodynamic stability). In this variation, the biosignal detection device 110 or an intermediary device (e.g., premise processing system 130, biosignal detection device tap, etc.) preferably anonymizes the data before transmitting the data to the remote computing system, but the patient data can be otherwise anonymized. The data (e.g., a single piece of data, a biosignal data window, a data stream, etc.) can optionally be uniquely identified by: a randomly-generated identifier, the biosignal detection device identifier, a hash of a patient identifier, or by any other suitable anonymized identifier. The anonymized identifier can be assigned by: the biosignal detection device, the intermediary device, the remote computing system (e.g., upon data receipt), or assigned at any other suitable time by any other suitable device.

The system 100 can optionally include a premise processing system 130 (e.g., virtual machine, premise server, etc.), which functions to record biosignal data (e.g., ECG data) and optionally perform any or all of: processing the data, windowing the data, presenting the data, or performing any other processing. The premise processing system 130 is preferably an on-premise virtual machine such as a tap on a biosignal detection device 110 (e.g., ECG monitor), desktop, or user device, but can additionally or alternatively be in the form of any other suitable local or remote computing system.

The premise processing system 130 transfers information (e.g., biosignal data, patient information, etc.) to and from the signal processor (e.g., cloud computing system). Additionally, the premise processing system 130 can transfer information (e.g., patient condition classifier) to an output (e.g., display) at the premises (e.g., healthcare facility), such as a computer at a central nursing station of an emergency room, and/or to a user device associated with healthcare personnel (e.g., sending a text message indicating hemodynamic stability to a physician).

The system 100 can further include memory 140 (e.g., storage), which functions to store any or all of: biosignal data (e.g., ECG data) of a given patient, patient information, models, algorithms, or any other suitable information. The memory 140 is preferably located in the cloud but can additionally or alternatively be local (e.g., on-premise). The memory 140 preferably includes a buffer (e.g., circular buffer, ring buffer, etc.) that stores the biosignal data, wherein the buffer can be sized to store patient data of a predetermined duration (e.g., 10 minutes of patient data), but can be otherwise configured. The memory 140 and/or secondary memory can optionally store higher-level patient data, such as the historical hemodynamic conditions for the patient (e.g., for all time, for a predetermined duration, etc.). However, the memory can be otherwise configured, structured, and/or used.

The system 100 can be configured to interface with, and optionally include, a display 150, which functions to display one or more outputs described below to a user, such as a nurse, physician, other healthcare personnel, or the patient. The display can include any or all of: a computer, monitor, user device, television, or other suitable display. In preferred variations, the display 150 includes a computer a central nursing station which displays a visual graphic indicating the progression of patient condition.

The system 100 is preferably configured to perform any or all of the method 200 but can additionally or alternatively be used to perform any other suitable method.

4. Method.

As shown in FIG. 2, the method 200 includes: receiving input data S210; determining a set of windows based on the input data S220; preprocessing each of the set of windows S230; processing each of the set of windows S240; determining a set of features for each of the set of windows S250; determining a hemodynamic condition for each window based on the set of features S260; and presenting the hemodynamic condition to a user S270. The method 200 can additionally or alternatively include any other suitable processes.

The method 200 functions to assess and continuously monitor the hemodynamic condition (e.g., stable, at risk, unable to be determined) of a patient, enabling earlier detection and subsequent intervention in the event of patient deterioration. The method 220 is preferably performed with any or all of the system 100 but can additionally or alternatively be performed with any other suitable system.

Variants of the method can leverage all or portions of the system or method disclosed in U.S. application Ser. No. 14/751,260 filed Jun. 26, 2015, which is incorporated herein in its entirety by this reference. However, any other suitable set of processes and systems can be used.

The method 200 can be performed for a patient in a healthcare facility (e.g., intensive care unit, emergency room, telemetry/step down care, etc.), but can additionally be performed for patients in a home setting, a mobile setting (e.g., ambulance), or in any other setting.

4.1 Method—Receiving Input Data S210

The method includes receiving input data S210, which functions to receive a biosignal with which to assess a patient's hemodynamic condition. The input data preferably includes a biosignal data stream (e.g., set of biosignal values, biosignal waveform, etc.) from a biosignal detection device; additionally, S210 can include receiving any other suitable inputs, such as those described above. The biosignal data stream is preferably received at a premise processing system operating on the biosignal detection device; additionally or alternatively, the biosignal data stream can be received at a local server (e.g., on-premise server of healthcare facility), remote server (e.g., cloud-computing system), or at any other suitable location. Further additionally or alternatively, input data can be received from a database, publication, study (e.g., clinical study), electronic medical records (EMR) system, electronic health records (EHR system), or from any other suitable source. The biosignal data stream can be received from healthy patients (e.g., clean signal stream) or from unhealthy patients (e.g., noisy signal stream, complicated signal stream, etc.), and the method is preferably configured to process data having any or all of: noise, missing data, inverted signals, drift (e.g., baseline drifted ECG), or any other complication.

Figure 12:
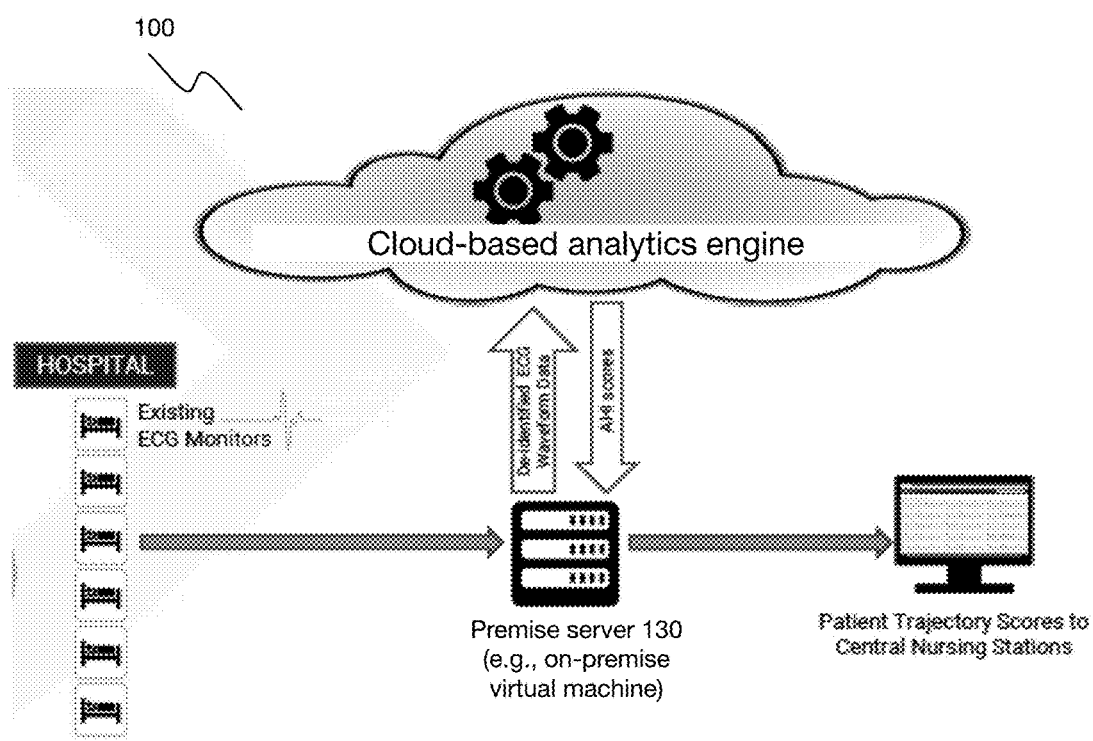
FIG. 12 is a schematic representation of a variation of the system.

In variations, an ECG signal stream is received from a lead (e.g., lead-II) of an ECG monitor through a premise processing system operating on the ECG monitor or communicatively connected to ECG monitor (e.g., as shown in FIG. 12). In these variations, the ECG monitor is preferably connected to a set of ECG electrodes, wherein the ECG electrodes are preferably attached to the patient. However, the ECG monitor can otherwise directly or indirectly monitor patient parameters.

The biosignal data stream is preferably received and monitored continuously. Alternatively, the biosignal data stream can be received with a prescribed frequency, for a predetermined duration, until a predetermined threshold is achieved (e.g., particular number of sequential "stable condition" classifications achieved), or can be received at any other suitable time.

S210 can include transmitting the input data to a remote server (e.g., cloud computing system). In these variations, S210 preferably includes de-identification (e.g., encrypting; locally mapping the dataset to a secondary identifier, such as the machine identifier, a randomly-generated identifier, the anonymized identifier, etc.; etc.) of patient identifiers prior to transmission, which can function to comply with one or more patient privacy protocols. Alternatively, the input data can be transmitted without alteration.

Figure 3:
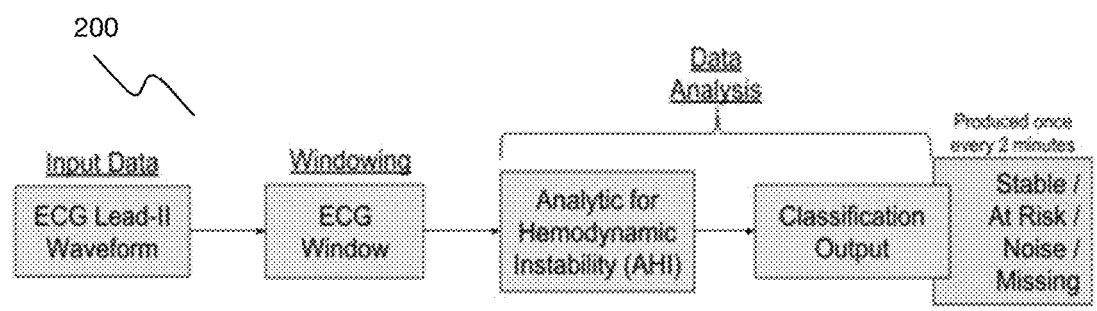
FIG. 3 is a schematic representation of a variation of the method.

In one variation, S210 includes receiving a continuous ECG waveform signal produced from lead-II of a standard application of an ECG monitor (e.g., as shown in FIG. 3), the signal having a sampling rate of 120 Hz or greater. Additionally or alternatively, S210 can include receiving any other suitable inputs at any sampling rate.

4.2 Method—Determining a Set of Windows Based on the Input Data S220

The method includes determining a set of windows based on the input data S220, which functions to separate the biosignal stream into a set of windows, each of which will be processed to determine a classification to indicate patient condition—or alternatively data quality—for the given window. S220 can additionally function to reorder input data (e.g., jumbled data), separate input data (e.g., from multiple patients, from multiple healthcare facilities, from multiple input data types, etc.), or otherwise modify the data.

S220 is preferably performed at a remote server (e.g., cloud computing system), but can alternatively be partially or fully performed at a local server, at an on-premise processing system (e.g., on-premise server, virtual machine, etc.), or at any other suitable location.

In preferred variations, S220 is performed after (e.g., in response to) S210 as each data packet of the biosignal data stream is received (e.g., asynchronously with a minimal delay, with a delay less than 1 minute, in substantially real time with S210, in real time with S210, etc.). Alternatively, S220 can be performed after a particular data packet size or duration has been received, after a predetermined amount of time has passed, or at any other suitable time.

The windowing of S220 is preferably performed through the application of a ring buffer (e.g., first in, first out buffer), which windows the data with a fixed window size and fixed frequency of delivery. Additionally or alternatively, S220 can include the application of any suitable windowing operation (e.g., tumbling window operation, hanning window operation, flattop windowing operation, uniform windowing operation, tukey windowing operation, exponential windowing operation, etc.) with any suitable buffer, window size duration (e.g., greater than 5 minutes, less than 5 minutes, between 2 and 10 minutes, fixed duration, variable duration, overlap between adjacent windows (e.g., greater than 2 minutes, less than 2 minutes, between 30 seconds and 4 minutes, fixed overlap between adjacent windows, variable overlap between adjacent windows, etc.), or any other windowing parameter.

Each window created from S220 is preferably fixed in length (time). In some variations, however, fixing the window in length is avoided. This can function to prevent one or more of the features determined in future steps from being dependent on heart rate and decreasing the specificity of the method.

Figure 4:
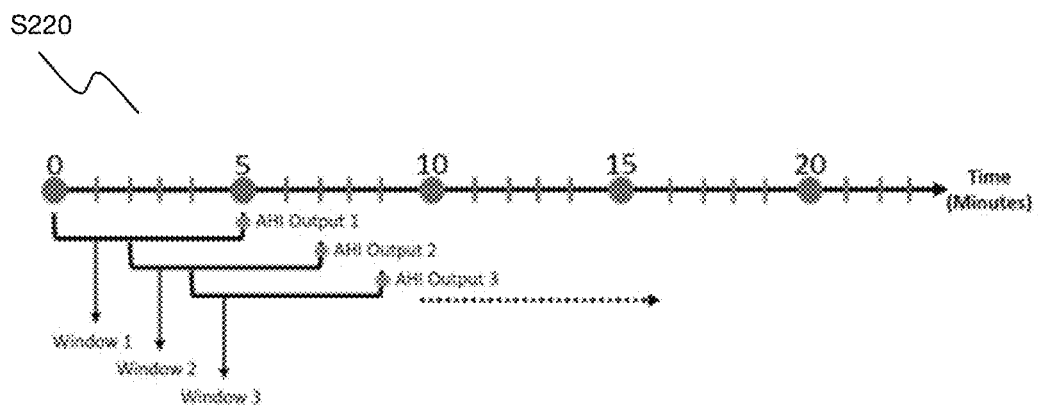
FIG. 4 is a schematic representation of a variation of a windowing process.

In one variation (e.g., as shown in FIG. 4), the window size is chosen to be five minutes in length, with each consecutive window produced at a frequency of once every two minutes.

The window size can optionally be determined (and/or dynamically adjusted) based on one or more physiological parameters, such as, but not limited to: the heart rate of a patient, the time between heartbeats of a single patient, the time between ECG peaks of an ECG data stream, an aggregated (e.g., average value, median value, maximum value, minimum value, etc.) time between peaks or beats, or any other suitable parameter.

In some variations, for instance, a window size is determined based on a number of heart beats, wherein the data stream is windowed such that each which contains 120 beats. Alternatively, any other suitable number of beats can be chosen.

The window size (e.g., as measured in time, as measured in number of beats, etc.) and overlap between windows is preferably constant among the set of multiple windows, but can alternatively be variable. In some variations, for instance, an overlap between windows is adjusted depending on patient condition (e.g., decrease time between sequential windows if patient condition deteriorates) or physiological parameters (e.g., increase window size when the heart rate decreases to maintain the same number of encompassed heart beats). However, the window size and/or adjacent window overlap can be otherwise determined.

The window size (e.g., length/time, number of beats, etc.) can additionally or alternatively be determined based on a parameter of a different biosignal, a parameter associated with the system (e.g., associated with transmission from the biosignal detection device), the healthcare facility, or any other suitable factor.

In addition to windowing, S220 can optionally include any number of data processing steps (e.g., once data is transmitted to a remote server, prior to transmitting to a remote server, etc.), which can function to reorder input data (e.g., when data packets are received at the remote server in a mixed order), sort data (e.g., separate a first patient's data from a second patient's data, separate based on healthcare facility, input type, etc.), filter, compress, or otherwise process the input data. These processing steps are preferably performed prior to windowing, but can additionally or alternatively be performed during or after windowing. In a specific example, for instance, when biosignal data is received at the remote server in a jumbled order, S220 can include sorting the data into an appropriate order (e.g., based on a timestamp from a biosignal detection device) prior to windowing.

In one variation, S220 includes determining a set of windows from an ECG signal stream based on a ring buffer (e.g., stored at a cloud computing system), which produces a set of five-minute-long windows, and wherein a new window is sent for processing (S230—initiated) every two minutes.

4.3 Method—Determining a Characterization of Hemodynamic Condition for Each Window For each window, the method includes characterizing the patient's hemodynamic condition, which functions to determine and enable continuous monitoring of patient hemodynamic stability. Determining the characterization for each window is preferably performed asynchronously (e.g., sequentially, with a single processor, etc.) with respect to other windows, but can alternatively be performed synchronously (e.g., partially synchronously, fully synchronously, batched, performed synchronously when an overlap period between consecutive windows has passed, performed with multiple processors, etc.). Determining the characterization preferably includes S230, S240, and 250 described below, but can additionally or alternatively include any other suitable processes.

4.4 Method—Preprocessing the Window S230

Figure 5:
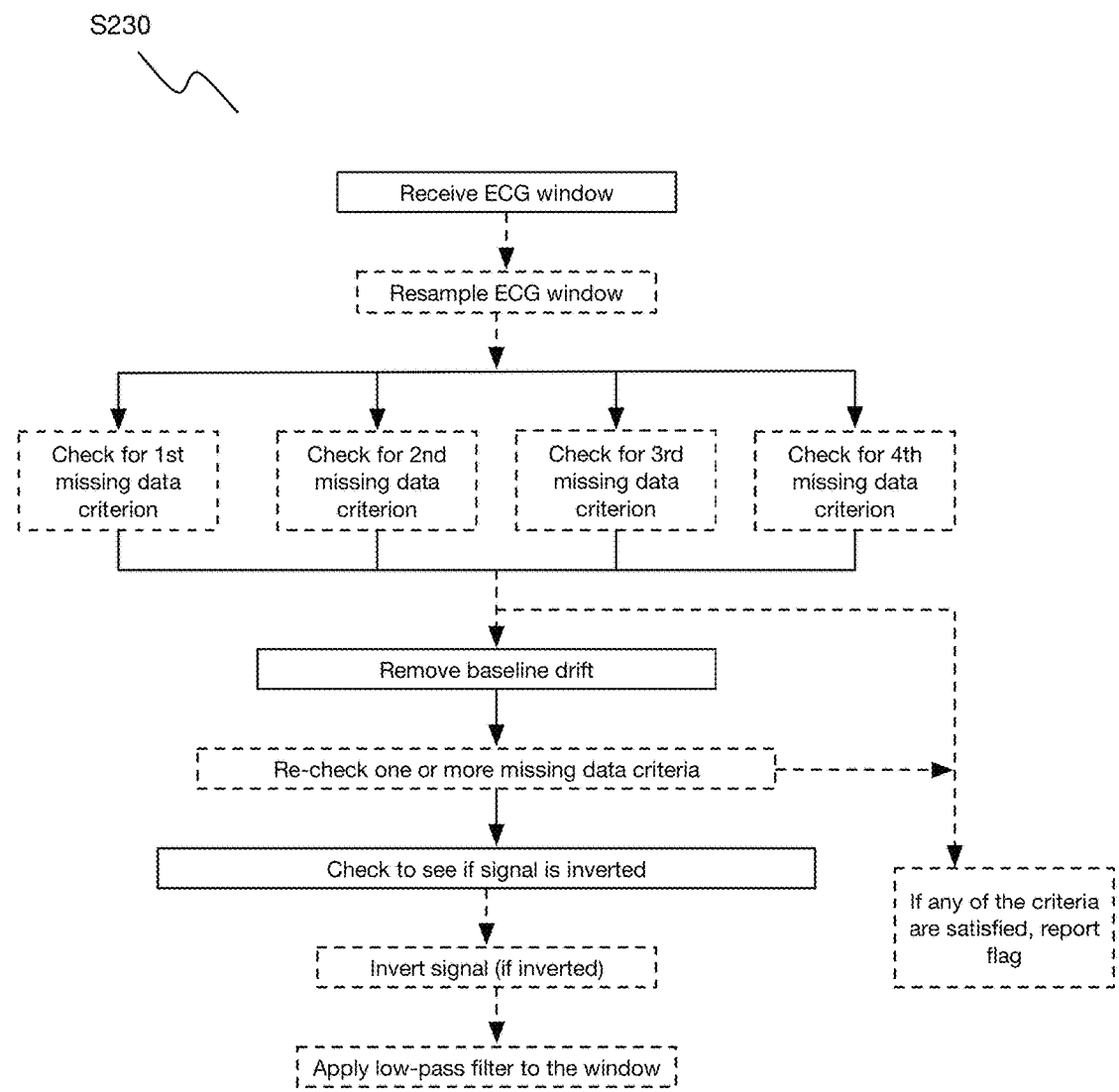
FIG. 5 is a schematic representation of a variation of preprocessing a window.

The method includes preprocessing the window S230 (e.g., as shown in FIG. 5), which functions to standardize each window irrespective of its source or sampling frequency. S230 can additionally or alternatively function to recognize issues with data quality of the window, such as missing data or excessive noise.

The input to S230 includes a window determined from S220, which is preprocessed through any or all of the following sub-processes.

4.5 Method—Resampling the Window S232

S230 can optionally include resampling the window S232. The resampling rate is preferably predetermined and fixed but can additionally or alternatively be determined based on a parameter (e.g., sampling rate, sampling frequency, original frequency, number of ECG spikes in the window, size of the window, etc.) associated with the incoming window.

In one variation, the resampling rate is set to a fixed value of 240 Hertz (Hz). In a specific example, this rate corresponds to a multiple (e.g., twice the value) of a number of samples contained in each second of incoming data (e.g., 120 Hz).

4.6 Method—Checking for Missing Data S234

S230 can further optionally include checking for the satisfaction of a set of data criteria S234, wherein if a predetermined number (e.g., one or more, a fraction, all, etc.) of the criteria are satisfied, a flag is reported. In preferred variations, reporting a flag initiates the termination of the remaining characterization processes as well as a labeling of the window with a classifier reflecting the missing data (e.g., labeled as "missing data", assigned a predetermined color for display in a visual graphic, etc.), but can alternatively include just one of these, the initiation of a trigger or prompt (e.g., prompt for additional data, initiation of a separate set of processing steps, etc.), identifying adjacent windows (e.g., preceding and/or following the problematic window) and piecing together the biosignal data for the problematic window (e.g., based on the data timestamps, etc.), or any other suitable action.

The set of criteria can include one or more criteria checking for missing data, which can be caused by anomalies in transmission. Preferably, multiple different missing data criteria are checked for, since the way in which missing values are imputed can vary depending on the data source (e.g., database, particular ECG monitor, healthcare facility server, etc.). Alternatively, checking for a single criterion (or no criteria) can be implemented. Additionally, any other criteria can be checked for.

In one variation, S234 includes checking for the following missing data criteria. A first data criterion includes checking for extreme overall biosignal values (e.g., ECG amplitudes), which are sometimes entered by a system (e.g., biosignal detection device) in the event that a data point is missing. In a specific example of this first data criterion, for instance, the method checks to see if an average ECG value in the window has an uncharacteristically high magnitude (e.g., less than −5000 or greater than 5000). A second data criterion includes checking for a predetermined subset (e.g., half of the data points, less than half of the data points, more than half of the data points, half of the window duration, etc.) of the biosignal data having a value of zero, which can indicate that that predetermined subset is missing from the dataset. In a specific example of the second data criterion, S234 can include checking to see half of an ECG signal (e.g., half of the data points, a duration of the window longer than half of the total window duration, etc.) has a value of zero. A third data criterion includes checking to see if the data include a non-numeric value (e.g., NaN) or a predetermined number or duration of non-numeric values. A fourth data criterion includes checking to see if the data include an infinite value. Additionally or alternatively, any other suitable criterion or criteria—corresponding to missing data or any other feature of the data—can be checked for during S234.

In variations having multiple criteria, the criteria can be checked in series, in parallel, or a combination of both. Furthermore, each of the criteria can be checked a single time or multiple times. In one example, for instance, the 2nd criterion is checked for twice during the method—once after the window is resampled and again after a baseline drift removal step, described below in S236.

4.7 Method—Removing Baseline Drift S236

S230 can further optionally include removing baseline drift S236 from the window, which can be performed after S232 and either during or after S234. This can function to reduce drift from the signal, which can be caused, for instance, by any or all of: heavy breathing of the patient, inconsistent electrode placement for ECG signals, and body movement of the patient. In some variations, removing baseline drift S236 is important, because if left in the signal, a future peak detection process can fail.

S236 preferably includes the application of a low frequency filter (e.g., high pass filter) with a preselected cutoff frequency and phase response; alternatively, any suitable filter(s) can be applied.

S236 can additionally or alternatively include the application of a fitting model, such as a linear fitting model (e.g., logistic regression-based model, moving average model such as a Savitzky-Golay model, etc.), a nonlinear fitting model (e.g., median filter model), or any other suitable model.

In one variation, S236 includes applying a best fit model to compute a best fit line for each window and then subtracting the best fit line from the signal.

For variations involving an ECG signal, S236 can include detecting QRS complexes of the signal to detect and characterize intervals of interest (e.g., PQ intervals). In a specific example, for instance, S236 includes minimizing a sum of squared errors and subtracting from the ECG signal (e.g., with an adaptive notch filter and blind source separation). However, baseline drift can be otherwise identified, managed, and/or removed.

4.8 Method—Checking for an Inverted Signal S238

S230 can optionally include checking for an inverted signal S238 (e.g., resulting from leads being incorrectly placed on the patient and subsequently switching the polarity and inverting the peaks). In one variation, for instance, S230 includes checking to see if the value of a data point in a first percentile with respect to magnitude (e.g., 95%, less than 95%, greater than 95%, etc.) of the ECG signal is greater than the value of a data point in second percentile with respect to magnitude, the second percentile smaller than the first percentile (e.g., 5%, less than 95%, etc.). In a specific example, for instance, S238 includes checking to see if an absolute value of a data point in the $95^{th}$ percentile is greater than an absolute value of a data point in the $5^{th}$ percentile. In the event that S238 determines that the signal is inverted, S238 can further include inverting the signal.

S230 can additionally or alternatively include any other suitable process(es). In some variations, for instance, S230 includes applying a low pass filter to the biosignal data configured to recognize and remove a particular issue with noise.

4.9 Method—Processing the Window S240

Figure 6:
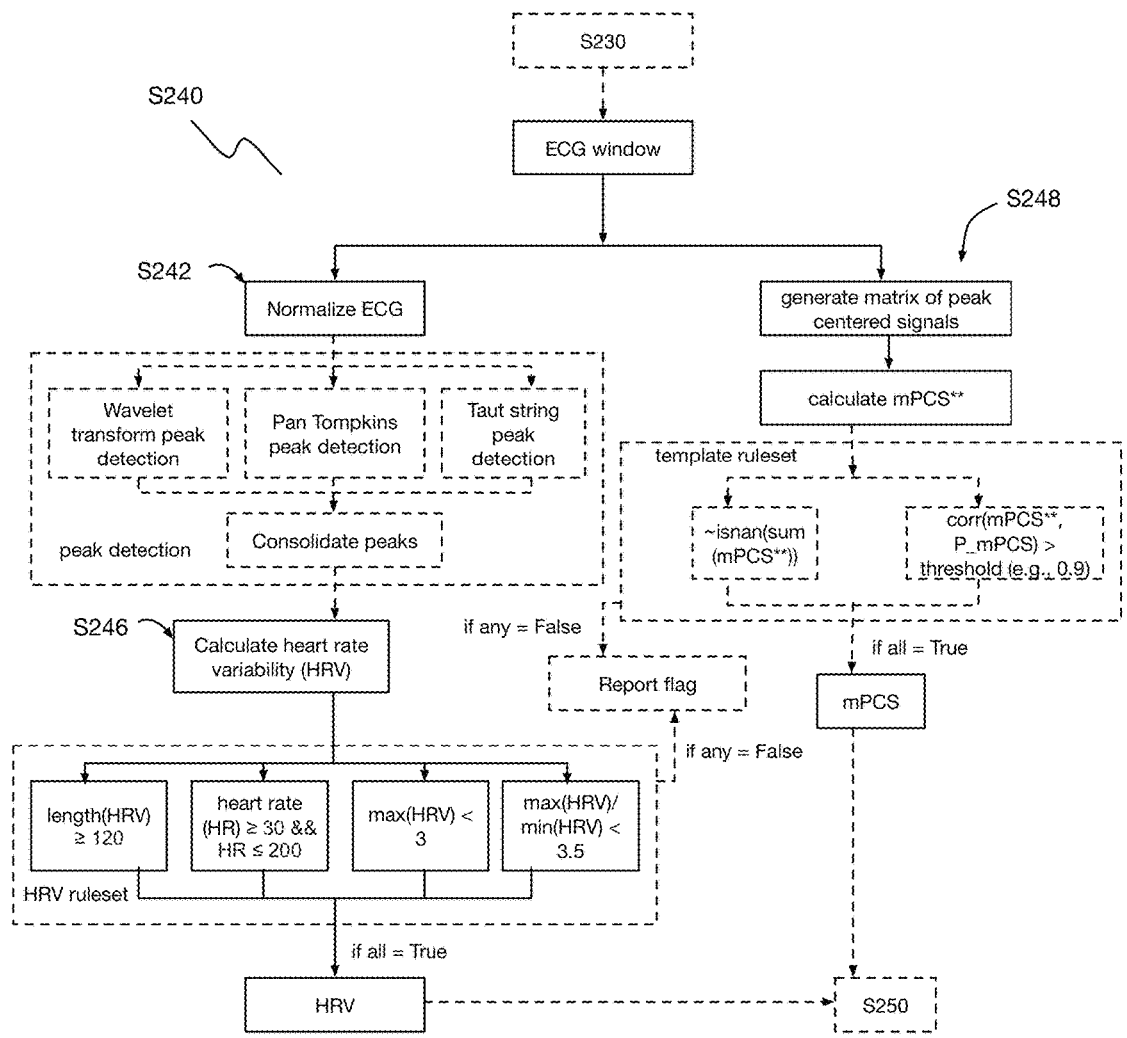
FIG. 6 is a schematic representation of a variation of processing a window.

The method 200 includes processing the window S240 (e.g., as shown in FIG. 6), which functions to analyze the signal quality by recognizing noise and artifacts inherent within the window of data. This can additionally function to determine whether or not to proceed with the remaining processes in characterizing the window. S240 can also function to handle a wide variety of noise (e.g., healthy subjects, non-healthy subjects) and edge cases that result from having ECG signals coming from a wide variety of patients (e.g., healthy, sick, etc.).

There are various ways in which noise can be introduced to the biosignal data, such as, but not limited to: spurious noise induced on the raw signal data by the sensor equipment, motion artifacts, power line interference, acquisition device quality, patient activity (e.g., breathing, coughing, moving, etc.), or other causes.

S240 preferably receives as an input the preprocessed window determined in S230 (e.g., checked to have no missing data, non-inverted, optionally preprocessed for a first set of noise types, etc.), but can additionally or alternatively receive any other suitable inputs.

4.10 Method—Normalizing the Window S242

S240 can optionally include normalizing the window S242, which can function to make the characterizations of a set of windows comparable with each other, accurate, and/or otherwise improved.

S242 is preferably performed with a normalization process that preserves the shape or set of features of the biosignal stream, such as any or all of the set of peaks (e.g., P peaks, Q peaks, R peaks, S peaks, etc.) in an ECG signal.

In one variation, each window is normalized based on a value (e.g., amplitude) of a peak (e.g., R peak) in the ECG signal. In a specific example, this includes: determining a median value of the signal, subtracting out the median value from the signal, and dividing the signal by the mean of the R-peak amplitudes.

In a second variation, S242 can additionally or alternatively normalize based on a time interval between peaks; this can function, for instance, to remove the effect of heart rate from one or more outputs (e.g., features) of the method 200.

In a third variation, S242 can further additionally or alternatively normalize without rescaling, with rescaling, based on a predetermined percentile of the data (e.g., $99^{th}$ percentile, less than $99^{th}$ percentile, greater than $99^{th}$ percentile, etc.), or through any other normalization process. However, the window can be otherwise normalized.

4.11 Method—Determining a Set of Peaks in the Window S244

The method includes determining a set of one or more peaks in the window S244, which functions to determine a heart rate variability (HRV) metric (e.g., conventional HRK) and a peak morphology metric, which can be instrumental in determining the set of features described below.

S244 is preferably performed with a set of multiple separate peak detection processes (e.g., algorithms), which are then compared and consolidated. Having this redundancy can function to robustly and confidently determine a set of peaks from the window. The set of peak detection processes preferably includes one or more custom or otherwise tailored processes to be used in the analysis of ECG signals but can additionally or alternatively use any other suitable processes for peak detection.

The peaks detected in S244 preferably include one or more ECG peaks (e.g., P, Q, R, S peaks), but can additionally or alternatively include any other peaks contained in a biosignal of the patient (e.g., peaks in a pulse oximeter signal).

In some variations, S244 includes the application of a wavelet transform peak detection process, which is not typically used for peak detection and had to be developed for this specific use case. The wavelet transform analysis can include: taking the ECG signal in the window and determining a set of wavelets in the hybrid time-frequency domain; determining one or more frequencies or a range of frequencies which correspond to the desired ECG peaks (e.g., QRS complex, PQRS complex, etc.); and selecting for the portions of the signal corresponding to those frequencies and removing the rest, thereby determining a set of wavelet transform peaks.

In some variations, S244 additionally or alternatively includes the application of a first-derivative-based peak detection process, further preferably a Pan-Tompkins peak detection process, which is a standard peak detection process used to determine a QRS complex of the ECG signal stream. Additionally or alternatively, any other suitable peak detection process (e.g., Hamilton-Tompkins) can be applied. The first-derivative-based peak detection process can include any or all of: applying a filter to the ECG signal stream to remove noise and remove signals outside of the QRS frequency band (e.g., applying a band pass filter, low pass filter, high pass filter, etc.); applying a derivative function to emphasize a shape (e.g., slope) of a feature (e.g., R-wave) in the ECG curve; applying a squaring function to enhance the frequency characteristics of the QRS complex; comparing any of these parameters with a threshold (e.g., patient-specific threshold) or applying any other suitable thresholding processes; applying a pulse train process; or applying any other suitable process(es).

In some variations, S244 additionally or alternatively includes applying a taut string peak detection process, which is not typically used for peak detection and had to be developed for this particular use case, which includes applying a taut string analysis—a mathematical method for determining changes in data—which is subsequently used to determine peaks.

Conceptually, the taut string analysis operates as if fitting a taut string to incoming data, which can function to de-noise incoming raw signal data and perform high fidelity compression of the data. Compressed signals can then be represented as a series of inflection points connected by a taut string rather than a set of thousands of time series data points. The time to completion may be linearly related to the size of the dataset (e.g., size of window and amount of data contained). Each time the string, tautly crossing data, encounters a boundary in the data, the string is turned back in generally the opposite direction. The result is a piecewise linear representation of the data, where each inflection point of the taut-string fit can be matched to a corresponding peak of the incoming raw ECG data. In some variations, a taut string algorithm relies upon use of an L1-norm to determine a rectilinear distance from which the ECG is analyzed.

A potential benefit of the taut string peak detection process is that it can allow for significant feature extraction for detection of nonlinear changes in the complexity of the received signal.

Additionally or alternatively, any other suitable peak detection process(es) can be applied.

In variations involving multiple peak detection processes, the processes can be performed in series (e.g., in a system using a single signal processor), in parallel, or in any suitable combination.

S244 can additionally include checking for an agreement between multiple peak detection processes (and/or with a peak detection process and a predetermined standard). In some variations, the peaks can be consolidated (e.g., averaged, matched, etc.) after agreement is reached. However, agreement can be otherwise used. In some variations, this is performed as follows. Each peak detection process produces a set of peaks each having an associated timestamp. These sets of peaks can then be compared with each other (e.g., by matching peak timestamps) to see if the sets are within a predetermined set of one or more error bounds (e.g., tolerance) of each other. The error bounds preferably include one or more predetermined constants but can alternatively be dynamically determined (e.g., based on the current window, a previous window, metadata associated with the window, etc.), variable, or otherwise determined. In one example, for instance, the error bound requires that peaks having the same timestamp must be within 5% or each other (95% correlation). Alternatively, any other suitable value (e.g., greater than 95% correlation, less than 95% correlation, etc.) can serve as an error bound. The total number of peak processes which have this agreement can then be determined and compared with a predetermined agreement threshold. In a specific example involving three peak detection processes, an agreement between 2 out of the 3 processes can be determined as suitable agreement. Alternatively, all processes implemented may be required to agree, a suitable fraction (e.g., half of the detection processes, greater than half, less than half, etc.) may be required to agree, the peak results can be weighted depending on the particular peak detection process used, or any other suitable agreement standard can be implemented.

In the event that agreement is not met, the method can optionally include any or all of: terminating the remaining processing steps, assigning a predetermined label to the window, repeating one or more peak detection processes, performing an additional peak detection processes, repeating the comparison process with a different set of parameters (e.g., different weightings of the results, different error bound, different comparison threshold, elimination of one or more sets of peaks, etc.), or any other suitable alteration.

If and/or once agreed sets of peaks are determined, S244 can include consolidating the agreed sets of peaks. Alternatively, S244 can include selecting one of the agreed sets of peaks (e.g., randomly, based on a weighting of the peak detection processes, based on a prioritized list of peak detection processes, etc.). In one variation, consolidating the agreed sets of peaks includes taking an average of the peaks having the same or a similar timestamp from each of the agreed processes. The timestamps can optionally be averaged as well. Alternatively, a median value, a minimum or maximum value, or any other suitable value from the peaks can be chosen.

In a specific variation of S244, S244 includes performing a wavelet transform peak detection process, a Pan-Tompkins peak detection process, and a taut string peak detection process; comparing the resulting sets of peaks with an error bound requiring a predetermined correlation (e.g., 95% correlation); checking to see if at least 2 out of the 3 sets of peaks agree; determining that at least 2 sets of peaks agree and taking the average of these peak values for each timestamp, thereby determining a consolidated set of peaks for the remaining processes of the method 200.

4.12 Method—Determining a Heart Rate Variability (HRV) Metric S246

The method includes determining a heart rate variability (HRV) metric S246 after the determination of a consolidated set of peaks in S244. The HRV metric preferably includes conventional HRV calculated according to standard calculations for HRV, such as determining a variability in time between the set of consolidated peaks. Additionally or alternatively, the HRV metric can include any other suitable parameter (e.g., heart rate) calculated in any suitable way.

With the HRV metric, S246 can additionally include checking for a set of HRV criterion, which functions to determine if the ECG signal in the window contains too much noise to be properly assessed and used in determining a patient hemodynamic condition. Preferably, multiple HRV criterion are checked for, as noise can manifest itself in various different ways in the signal, but alternatively a single criterion can be used.

A first HRV criterion can check to see if the number of peaks is above a predetermined threshold (e.g., related to the sampling frequency, related to the original number of peaks in the raw window, etc.). In a specific example, the first HRV criterion checks to see if the window contains 120 peaks. Alternatively, any other threshold can be used (e.g., greater than 120 values, less than 120 values, etc.).

A second HRV criterion can check to see if the heart rate itself is within a predetermined set of bounds. In a specific example, for instance, the second HRV criterion can check to see if the heart rate (e.g., average heart rate) is greater than or equal to 30 beats per minute and less than 200 beats per minute. Alternatively, any other threshold can be used.

A third HRV criterion can check to see if a maximum HRV value is below a predetermined threshold. In a specific example, the third HRV criterion checks to see if the maximum variability between adjacent peaks is less than 3 seconds. Alternatively, any other threshold can be used (e.g., less than 5 seconds, less than 2 seconds, etc.).

A fourth HRV criterion can check to see if any significant gaps (e.g., resulting from a heart arrhythmia) are present. In a specific example, for instance, the fourth HRV criterion can check to see if a ratio of the maximum HRV to the minimum HRV is below 3.5. Alternatively, any other threshold can be used (e.g., greater than 3.5, less than 3.5, etc.).

Additionally or alternatively, any other suitable HRV criteria can be checked for. In variations having multiple criteria, they can be checked for in series, in parallel, or in any suitable combination.

In preferred variations, if any or all of a set of HRV criteria are satisfied, the characterization portion of the method is terminated. Further preferably, a label is assigned to the window indicating that the window corresponds to noisy data. Additionally, windows of noisy data can optionally be further analyzed to determine and present a more detailed indication of the nature of noise (e.g., type of noise, noise source, predicted noise source, etc.) present within the biosignal. Additionally or alternatively, the method can continue as normal, or any other action can be triggered (e.g., repeating an HRV calculation, determining another heart rate parameter, etc.).

In one variation, S246 includes determining the HRV based on the set of consolidated peaks; applying each of the $1^{st}$, $2^{nd}$, $3^{rd}$, and $4^{th}$ data criteria; determining that at least one of the criteria are satisfied; assigning a label of "noisy data" to the window; and terminating the characterization portion of the method.

4.13 Method—Determining a Morphology Metric S248

S240 includes determining a morphology metric (e.g., ECG morphology metric), which functions to assess the morphology (equivalently referred to as shape) of the set of biosignal peaks (e.g., consolidated ECG peaks) and optionally the regions immediately adjacent to the peaks, or any other suitable regions of the biosignal data. Since morphology is patient-specific, S248 functions to enable proper tracking of patient condition between windows. In some variations, for instance, assessing the regions (which correspond to a set of indices, wherein each of the indices can include a signal amplitude and a timestamp) immediately preceding and following each peak can help determine and monitor patient-specific progression.

S248 is preferably performed after peak detection in S244 (e.g., with the set of consolidated peaks) and can be performed in series with S246 (e.g., before, after, etc.), in parallel with S246, in place of S246, in parallel with S242, or otherwise performed.

S248 can optionally further include determining a morphology metric for a current window and comparing with a corresponding morphology metric for a set of one or more previous or following windows.

In one variation, the morphology metric includes a mean of peak-centered signals (mPCS) for the window. For these variations, determining the morphology metric can include generating a matrix of peak-centered signals and determining an mPCS from the matrix. The mPCS can then optionally be added to a second matrix (e.g., which includes mPCS values from each window), compared with previous mPCS values, or otherwise used in the determination of a set of features described below.

In some variations, the mPCS is determined through any or all of the following processes. First, the consolidated peaks for a window can be used to form a matrix, referred to as the matrix of peak-centered signals. In one example, the matrix of peak-centered signals can be determined by selecting a predetermined set of indices (e.g., 50 indices, less than 50 indices, greater than 50 indices, etc.) preceding each of a set of peaks (e.g., 120 peaks, less than 120 peaks, greater than 120 peaks, all peaks in the window, a subset of peaks in the window, etc.), further preferably consolidated peaks, identified in a given window and a predetermined number of indices (e.g., same number as the predetermined number of indices preceding, 50 indices, less than 50 indices, greater than 50 indices, etc.) following each of the set of peaks. Alternatively, only indices preceding each peak can be selected, only indices following each peak can be selected, or any other indices can be selected. Each of the set of peaks and their corresponding indices is herein referred to as a peak-centered signal. Preferably the same number of indices are selected for each peak, but alternatively any number can be chosen for each peak. The peaks and each of their sets of preceding and/or following indices are than arranged in a matrix, herein referred to as the matrix of peak centered signals.

A mean of peak-centered signals can then be calculated for each window from the matrix of peak-centered signals by averaging the values (e.g., amplitudes, timestamps, both amplitudes and timestamps) of those peak-centered signals whose correlation to at least a predetermined fraction (e.g., half, greater than half, less than half, etc.) of the other peak-centered signals (e.g., the remaining 119 peak-centered signals in the case of 120 total peak-centered signals) is above a predetermined threshold (e.g., 0.5, at least 0.5, less than 0.5, greater than 0.5, greater than 0.75, 0.9, less than 0.9, greater than 0.9, between 0.5 and 0.99, etc.). The mean of peak-centered signals is preferably a matrix having an averaged peak value and an averaged set of indices, but can additionally or alternatively include any other suitable information, or be further processed (e.g., to form a scalar value) in any other suitable way.

Additionally, any other suitable information can be used to form the matrix of peak-centered signals and/or the mean of peak-centered signals, such as the width of each peak, one or more timestamps associated with each peak, one or more slopes of each peak, or any other parameters corresponding to peak morphology. With this matrix, the mPCS is calculated and used in the determination of a set of features, as described below.

Determining the mPCS can additionally include checking for satisfaction of a set of criteria, wherein if any of the criteria are not satisfied (e.g., false), a flag is reported (e.g., as shown in the template ruleset of FIG. 6). Additionally or alternatively, a flag can be reported in the event that one or more criteria are satisfied (e.g., true). In some variations, reporting a flag cancels the remaining characterization portion of the method. Additionally or alternatively, reporting a flag can include sending an alert, assigning a label to the window, or any other suitable action. These criteria can include any or all of: checking to see if the mPCS is a number; checking to see if the mPCS has a value (e.g., is not empty); checking to see if there is appropriate correlation (e.g., 0.9 or greater, greater than 0.9, between 0.8 and 0.99, between 0.5 and 1, at least 0.5, etc.) between an mPCS for a particular window and an mPCS for a different (e.g., previous) window (e.g., as indicated as P_mPCS in FIG. 6); and any other suitable criteria. In some variations (e.g., as shown in FIG. 6), an intermediate mPCS (shown as mPCS) is found and referred to as such prior to determining that it satisfies the set of criteria. In a specific example as shown in FIG. 6, the mPCS is checked to make sure that it contains one or more numeric values, is not empty, and has a correlation of at least 0.9 with a previous window; in the event that any of these criteria are not satisfied, a flag can optionally be reported.

In some variations, the way in which a flag is reported depends on the type of criterion and/or whether or not it is satisfied. In a specific example, a first flag is reported if a first predetermined sub-set of criteria (e.g., seeing if mPCS is a number, seeing if mPCS has proper correlation with P_mPCS, etc.) are not satisfied, and a second flag is reported if a predetermined second sub-set of criteria (e.g., seeing if P_mPCS is empty) are satisfied. Reporting the first flag can result in a first outcome (e.g., discarding the window, labeling the window, stopping the method, etc.) whereas reporting the second flag can result in a second outcome (e.g., further processing the window, different outcome than the first outcome, etc.). Alternatively, the criteria can all be checked in the same way, reporting flags can result in a single outcome, or criteria can be checked for and/or reported in any other suitable way.

4.14 Method—Determining a Set of Features for the Window S250

The method includes determining a set of features for the window S250, which are subsequently used to determine a classification of patient condition (e.g., hemodynamically stable, hemodynamically at risk (e.g., at risk for being currently unstable, at risk for being unstable in the future, etc.), etc.).

Each of the set of features is preferably determined based on at least one of: the HRV metric, the morphology metric, or any other parameters included in the biosignal data. Additionally or alternatively, the set of features can be determined based on any other suitable data.

The set of features preferably includes both patient agnostic features (Group 1 features) as well as patient specific features (Group 2 features) but can alternatively include a single type of features. Within these feature types, the set of features further preferably include features determined through a time analysis of the input data and features determined though a frequency domain analysis of the input data, but the set of feature can additionally or alternatively include features determined through any suitable analysis of the data (e.g., hybrid time-frequency analysis).

The patient agnostic features are preferably determined based on the HRV metric, and include one or both of: a set of time-series statistics features and a set of frequency domain features. In some variations, the set of time-series statistics features is split into a first and second subset, wherein the first subset (e.g., 5 features, less than 5 features, greater than 5 features) is determined based—at least in part—on a time series analysis of the HRV metric, whereas the second subset (e.g., 4 features, less than 4 features, greater than 4 features, etc.) is determined based—at least in part—on a taut string transform of the biosignal data and the HRV metric. The set of frequency domain features can also be split into multiple subsets, wherein the first subset (e.g., 3 features, less than 3 features, greater than 3 features, etc.) is determined based—at least in part—on a frequency domain analysis of the HRV metric, whereas the second subset (e.g., 2 features, less than 2 features, greater than 2 features, etc.) is determined based—at least in part—on a taut string transform of the biosignal data and the HRV metric. Additionally or alternatively, any other subsets of features can be determined.

In one variation, determining the subset of Group 1 features determined through a taut string transform includes: calculating taut string L1-norm features based on HRV and generating piecewise linear estimates, wherein the piecewise linear estimates include any or all of: features based on the number of nodes in the window divided by the number of beats in the window, features based on the number of points of inflection contained in an interval divided by number of beats in window, and features based on a total variation between the original signal and the taut string estimation, normalized by at least the number of beats in the window. Alternatively, the taut string transform can be otherwise applied, resulting in any other suitable features.

The patient specific features function to carry knowledge over time, establishing a sort of memory between windows. This enables changes and progression to be detected within the context of a specific patient.

The patient specific features are preferably determined based on the morphology metric (e.g., mPCS), and include one or more of: a set of QRS outliers (e.g., 1 feature, greater than 1 feature, etc.), a set of morphology features (e.g., 2 features, less than 2 features, greater than 2 features, etc.), and a set of QRS amplitude features (e.g., 1 feature, greater than 1 feature), which can function to indicate how a biosignal (e.g., ECG biosignal) is evolving over time. Additionally or alternatively, any other suitable patient specific features can be determined.

Figure 7:
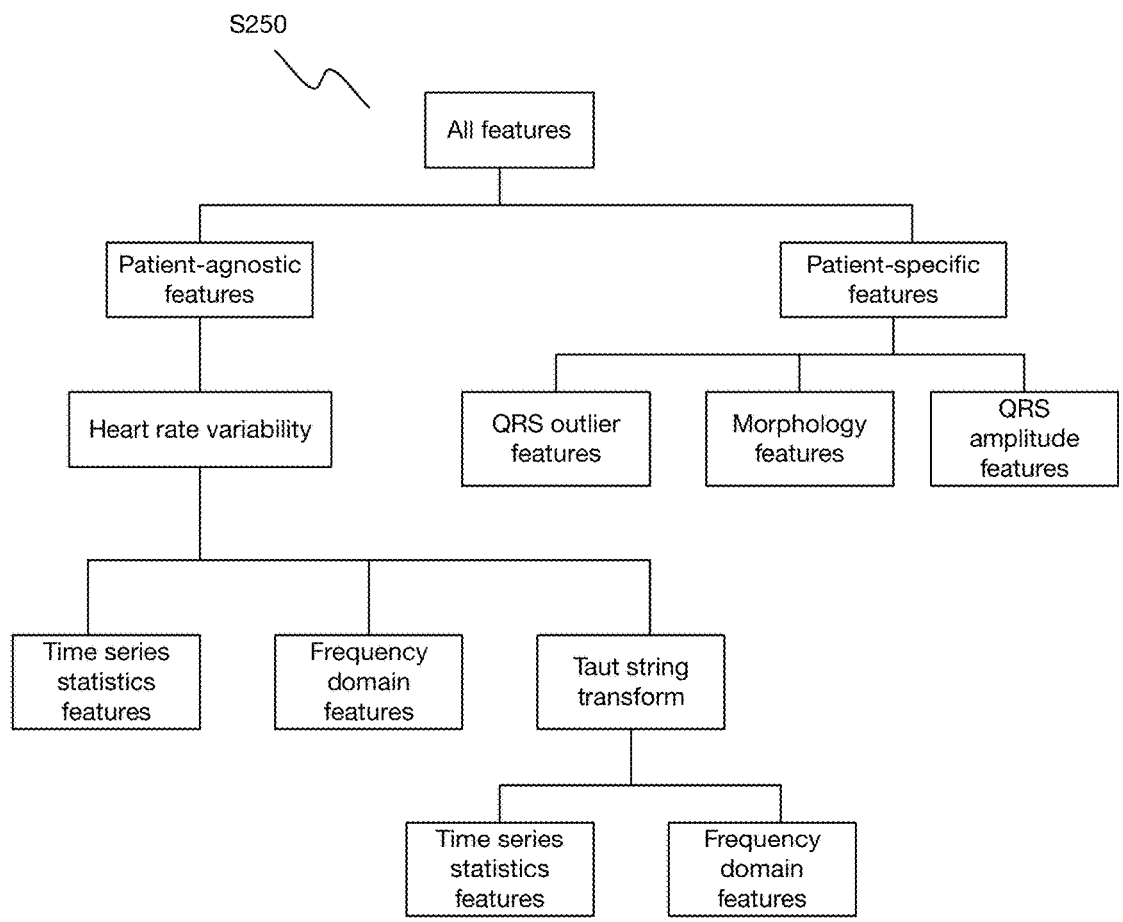
FIG. 7 is a variation of a set of features used to determine a patient condition.

In one variation, as shown in FIG. 7, determining the set of features includes determining all of: time series statistics features determined from HRV (e.g., 5 features), frequency domain features determined from HRV (e.g., 3 features), time series statistics features determined from the application of a taut string transform and HRV (e.g., 4 features), frequency domain features determined from the application of a taut string transform and HRV (e.g., 2 features), QRS outlier features (e.g., 1 feature), morphology features (e.g., 2 features), and QRS amplitude features (e.g., 1 feature). In a specific example, 18 total features are determined. Alternatively, any other suitable number of features can be determined (e.g., between 5 and 30, between 15 and 20, between 10 and 20, less than 5, greater than 30, etc.).

S250 can additionally including choosing the set of features described above, and determining which set of features to find values for. This can be determined through the application of one or more rules, deep learning models (e.g., neural network, convolutional neural network, etc.), further preferably deep learning models trained through supervised learning, a support vector machine model, a classification via regression model, decision tree learning algorithms, clustering algorithms, feature selection algorithms, or any other suitable set of models and algorithms. The models are preferably trained on data from both sick and healthy patients (e.g., labeled data, unlabeled data, etc.) to ensure that the resulting features result in accurate predictions for all or most use cases. Alternatively, the models can be trained on specific datasets (e.g., to detect the presence of specific instability triggers, for instance).

Narrowing in on the final set of features can include performing a cross-correlation/cross-validation analysis on the potential features, to determine a set which is consistently robust yet includes minimal overlap between features.

Choosing the set of features can additionally include comparing the values determined from the set of features (and/or the resulting condition) with clinical study results to ensure that set of features appropriately predicts patient condition.

4.15 Method—Determining a Hemodynamic Condition for Each Window Based on the Set of Features S260

The method includes determining a hemodynamic condition for each window based on the set of features S260, which functions to produce a classification of patient condition based on the set of features. S260 is performed with the values for the set of features determined in S250.

Figure 8:
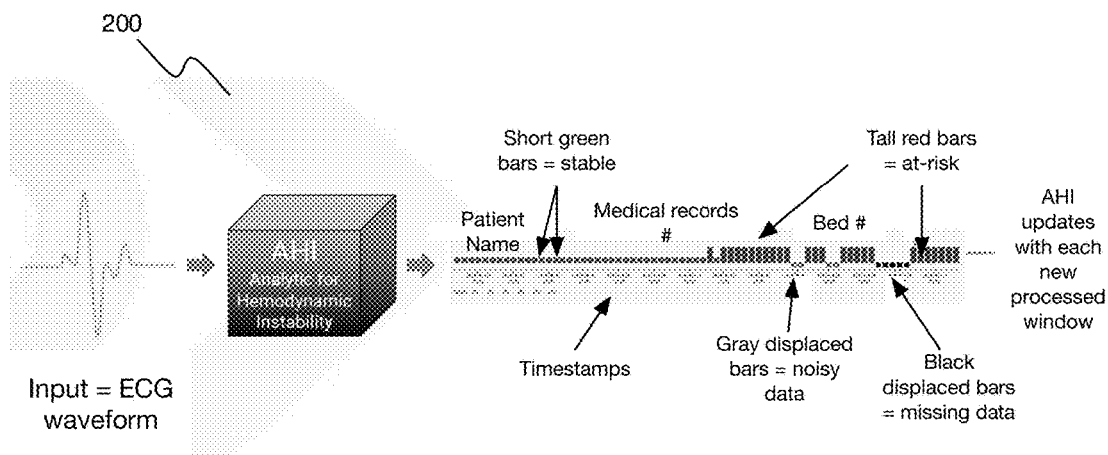
FIG. 8 represents a variation of the method.

S260 is preferably performed through the application of one or more models or algorithms. Examples of models or algorithms that can be used to determine the hemodynamic condition can include one or more: heuristics, rule sets, neural networks (e.g., convolutional neural network, deep neural network, recurrent neural network, etc.), classifiers (e.g., support vector machines, decision trees boosted trees, random forest, neural networks, nearest neighbors, etc.), regression models (e.g., linear regression, regression trees, lasso regression, multivariate regression, etc.), clustering algorithms, or any other suitable set of models and algorithms. The hemodynamic condition models are preferably trained on data from both sick and healthy patients (e.g., labeled data, unlabeled data, etc.) to ensure that the resulting features result in accurate predictions for all or most use cases, but can be trained on the patient data (e.g., exclusively or in combination with other patients), or otherwise determined. The set of features can be weighted, unweighted, ranked, or otherwise prioritized during the analysis. The set of features are preferably analyzed such that they output a hemodynamic stability score (e.g., analytic for hemodynamic instability [AHI] as shown in FIG. 8), wherein the value of the score (e.g., in comparison with a threshold) determines whether the patient's hemodynamic condition is stable or at risk. Additionally or alternatively, the outputs of each feature can be individually analyzed (e.g., compared with a threshold), wherein the results of these analyses are used (e.g., tallied) to determine a score used to classify the patient's hemodynamic condition. Additionally or alternatively, the feature values can be fed into one or more classifiers that output a hemodynamic condition class (e.g., stable/at risk) and/or probability per hemodynamic condition class. However, the patient's hemodynamic condition can be otherwise determined.

The frequency at which the set of classifications is produced is preferably determined based on a parameter of the windowing process (e.g., equal to frequency at which consecutive windows are processed, a larger frequency than that of windowing, etc.).

The resulting classification of hemodynamic condition, specifically hemodynamic stability, can be binary or non-binary. In binary variations, the resulting hemodynamic condition indicates whether the patient is stable or at risk, and can subsequently including assigning a label to the corresponding window reflecting this classification (e.g., "stable", "at risk", "unstable", etc.). In alternative non-binary variations, the score can be mapped to a spectrum of hemodynamic condition (e.g., corresponding to a predicted time until instability).

The set of classifications preferably additionally includes those described above, which were determined above based the application of one or more elimination criteria (e.g., "missing data", "noisy data", etc.).

4.16 Method—Presenting the Hemodynamic Condition to a User S270

The method includes presenting the hemodynamic condition to a user S270, as indicated through the classification (e.g., stable, at risk, missing data, noisy data, etc.) of each window. This functions to allow for the continuous monitoring of the patient's hemodynamic condition.

A user can include any or all of: a physician, nurse, doctor, healthcare facility administrator or other worker, patient, or any other individual.

The classifications determined above can be presented to the user in a visual format, which can integrate easily with current healthcare facility equipment and protocols, as well as provide easily-digestible, non-disruptive information. The classifications can be displayed on any suitable display (e.g., monitor, screen, etc.), such as, but not limited to: nurse's workstation display, emergency room workstation display, user device (e.g., tablet, mobile phone, etc.), or any other suitable display. However, the classifications can be represented in: audio format (e.g., beep when a predetermined hemodynamic condition, such as "at risk," is determined), haptic format (e.g., vibrate an actuator, such as on a beeper or a smartwatch, when the predetermined hemodynamic condition is determined), or in any other suitable format.

Figure 9:
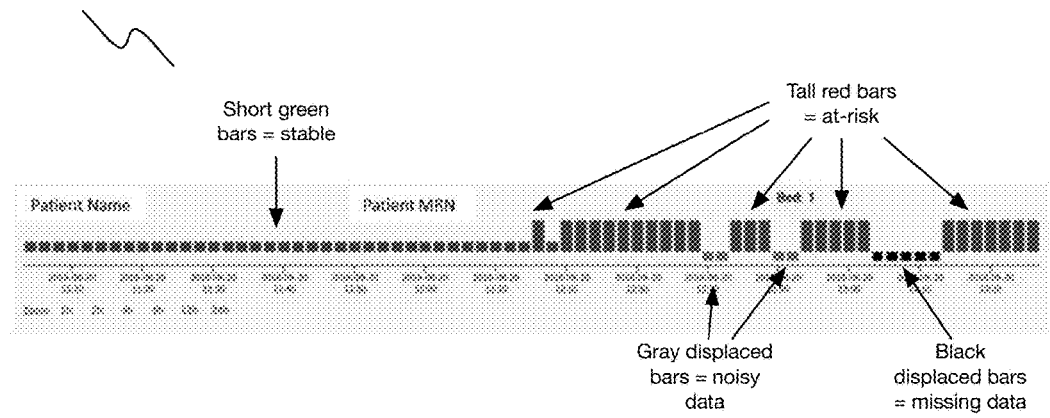
FIG. 9 represents a variation of a visual graphic to view and monitor a set of patient condition classifications for a single patient.
Figure 10:
FIG. 10 represents a variation of a visual graphic to view and monitor a set of patient condition classifications for multiple patients.

The classifications are preferably displayed as a continuous record (e.g., routinely-updated, continuously-updated, etc.), showing a temporally advancing progression of patient condition. Any or all of: color, shape, size (e.g., bar height), and trends can be used to indicate the particular hemodynamic classification. The display can further include multiple patient views (e.g., as shown in FIG. 10) as well as single patient views (e.g., as shown in FIG. 9). The multiple patient views can function, for instance, to provide unit level assessment for rapid patient care prioritization, whereas the single patient view can facilitate detailed exploration of trends of a given patient's hemodynamic status.

S270 can additionally or alternatively include initiating an alert or alarm in response to a predetermined trigger, such as but not limited to: a duration or number of windows having a certain classification (e.g., at risk, missing data, etc.); a change in classification between windows (e.g., stable to at risk, at risk to stable, etc.); noisy data (e.g., to indicate that lead placement should be checked, to indicate a suspected arrhythmia, to indicate suspected ectopic beats, etc.); missing data (e.g., to trigger nurse to check on patient); or any other suitable trigger. Alternatively, these triggers can be initiated prior to S270 (e.g., when missing data is first identified). The alert or alarm can be: audio, visual (e.g., a blinking light), a notification (e.g., an email, an SMS message, etc. with patient information), haptic, or be presented in any other suitable format.

In one variation, a visual graphic (e.g., as shown in FIG. 9) presented at a display (e.g., nurse's workstation) includes a record of patient condition classification bars (or other visual indicators), which is updated with a new bar after the processing of each window. The bars can vary in height, color, size, brightness, or otherwise to appropriately and efficiently indicate the patient's condition, as well as detect any changes to it. In a specific example wherein the potential hemodynamic condition classifications indicate patient stability, patient instability, noisy data, and missing data, the bars having the following appearance: short, green bars indicate stability, tall red bars indicate instability, gray bars vertically displaced from the red and green (e.g., arranged beneath) indicate noisy data, and black bars vertically displaced from the red and green indicate missing data. Alternatively, the classifications can be otherwise displayed.

S270 can additionally include re-identifying the patient (e.g., prior to presenting a visual graphic, in conjunction with presenting a visual graphic, etc.), automatically informing and/or initiating a treatment option (e.g., drug delivery, drug selection, etc.) based on the classification results.

4.17 Method—Variations

In one variation, the system 100 includes: a premise processing system (e.g., premise server) operating on an ECG monitor and a signal processor operating at a remote computing system, wherein the premise processing system (e.g., premise server) receives ECG data from the ECG monitor, transmits the information to the signal processor, wherein the ECG data is processed to determine a hemodynamic condition classification, which is sent back to an on-premise display for viewing by a healthcare provider.

Additionally or alternatively, the system 100 can include any other suitable components.

Figure 11:
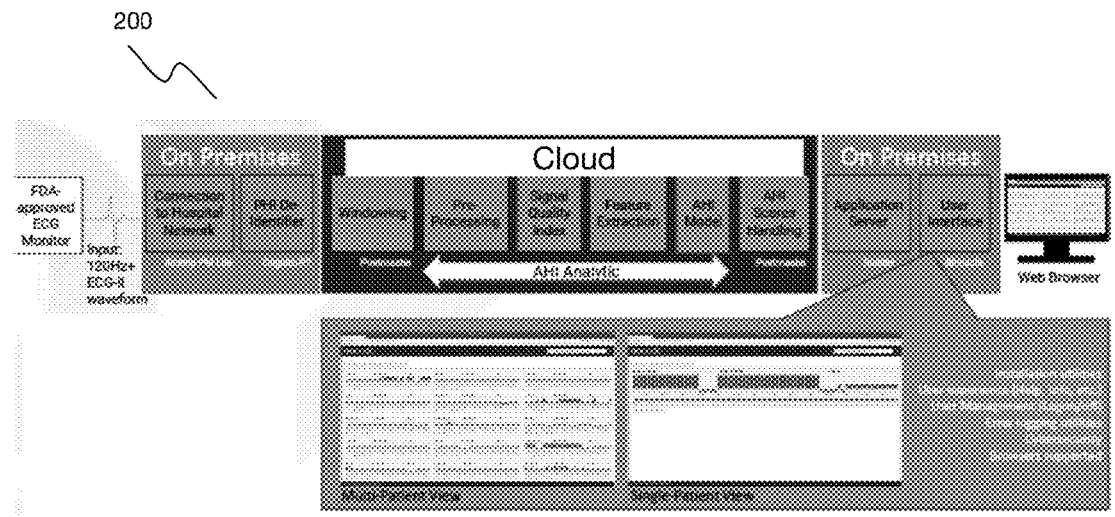
FIG. 11 is a schematic representation of a variation of the method.

In one variation (e.g., as shown in FIG. 11), the method 200 includes any or all of: receiving an ECG lead-II waveform from an ECG monitor at a premise processing system executing on the ECG monitor; de-identifying the ECG waveform data; transmitting the de-identified ECG waveform data to a cloud analytics engine (e.g., powered by Amazon Web Services™ [AWS™]); arranging the ECG waveform data into a proper temporal order; windowing the ECG waveform data based on a ring buffer having a fixed window size (e.g., 5 minutes) and a fixed overlap between windows (e.g., 2-minute overlap); for each window, resampling the window (e.g., to a resampling rate of 240 Hertz); checking for a set of missing data criteria (e.g., $1^{st}$, $2^{nd}$, $3^{rd}$, and $4^{th}$ missing data criteria); in the event that any of the missing data criteria are satisfied, ending the characterization of the window and assigning a label of "missing data" to the window; removing baseline drift from the window; checking for an inverted ECG signal and correcting if an inverted signal is detected; re-checking for one or more missing data criteria; removing a subset of noise through the application of a low-pass filter; normalizing the window; determining a set of consolidated peaks through the application of multiple peak detection processes (e.g., wavelet transform peak detection, Pan-Tompkins peak detection, and taut string peak detection, determining an agreed set of peaks from the multiple processes, and averaging the peaks to determine the consolidated peaks; determining the HRV; checking for a set of noise criteria (e.g., $1^{st}$, $2^{nd}$, $3^{rd}$, and $4^{th}$ noisy data criteria); in the event that any of the noisy data criteria are satisfied, ending the characterization of the window and assigning a label of "noisy data" to the window; determining a morphology metric; choosing a set of features; determining the values for the set of features to determine a hemodynamic condition; determining a classification based on the score; and presenting the classification to a user through a visual graphic. Additionally or alternatively, the method 200 can include any other suitable step(s).

In one variation, the system 100 and/or method 200 can be implemented using any or all of the systems and/or methods described in U.S. application Ser. No. 14/751,260, filed 26 Jun. 2015, now issued as U.S. Pat. No. 9,974,488, which is incorporated herein in its entirety by this reference.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method for the continuous monitoring of a hemodynamic condition of a patient, the method comprising:
receiving an electrocardiogram (ECG) signal stream from an ECG monitor, the ECG signal stream comprising a time series of ECG signals;
determining a set of windows based on the ECG signal stream, each window comprising a segment of the ECG signal stream;
determining a label for each of the set of windows, comprising:
when ECG signals are missing from the window, assigning a first label to the window;
when ECG signals are not missing from the window, determining a set of consolidated ECG peaks based on the ECG signals within the segment of the ECG signal stream, wherein determining the set of consolidated ECG peaks comprises:
applying a set of multiple peak detection processes to the ECG signals to determine multiple sets of peaks;
comparing the multiple sets of peaks with each other and with a predetermined agreement threshold to determine an agreed set of peaks;
consolidating the agreed set of peaks to determine the set of consolidated ECG peaks;
determining a heart rate variability based on the consolidated ECG peaks;
determining an ECG morphology metric based on the consolidated ECG peaks;
checking the ECG signals for a set of criteria;
when at least one of the set of criteria is satisfied, assigning a second label to the window;
when none of the set of criteria is satisfied:
determining a set of hemodynamic stability feature values based on the heart rate variability metric and the ECG morphology metric; and
assigning one of a third and fourth label to the window based on the set of hemodynamic stability feature values; and
displaying a visual graphic for each of the set of windows at a display of a healthcare facility, wherein each visual graphic is associated with the label assigned to the respective window.

2. The method of claim 1, wherein the set of windows comprises a set of overlapping windows.

3. The method of claim 2, wherein each of the set of windows has a length of five minutes.

4. The method of claim 3, wherein each consecutive window in the set of windows is produced at a frequency of once every 2 minutes.

5. The method of claim 1, wherein determining the label further comprises resampling the window and removing a baseline drift.

6. The method of claim 1, wherein displaying the visual graphic comprises displaying a set of bars, each of the set of bars corresponding to a window, wherein the set of bars are arranged in a temporal order and assigned a color depending on the label assigned to the corresponding window.

7. The method of claim 1, wherein the ECG signal stream is stored in a ring buffer.

8. The method of claim 1, wherein the ECG morphology metric comprises a mean of the set of consolidated ECG peaks.

9. The method of claim 1, wherein the set of hemodynamic stability feature values are determined at least in part from a set of outliers of a QRS complex of the ECG signal stream and a set of amplitudes of the QRS complex.

10. The method of claim 9, wherein the set of hemodynamic stability feature values comprises between 15 and 25 hemodynamic stability feature values.

11. The method of claim 1, wherein the set of multiple peak detection processes comprises a wavelet transform.

12. The method of claim 1, wherein the set of multiple peak detection processes comprises three peak detection processes, and wherein the predetermined agreement threshold requires an agreement between at least two peak detection processes.

13. A method for the continuous monitoring of a hemodynamic condition of a patient, the method comprising:
receiving an electrocardiogram (ECG) signal stream from an ECG monitor;
determining a set of windows based on the ECG signal stream;
for each of the set of windows, determining a label for the hemodynamic condition, wherein determining the label comprises:

determining a set of consolidated ECG peaks based on the window;

determining a heart rate variability based on the consolidated ECG peaks;

determining an ECG morphology metric based on the consolidated ECG peaks;

determining a set of hemodynamic stability feature values based on the heart rate variability metric and the ECG morphology metric; and determining the label for the window, indicating the hemodynamic condition of the patient, based on the set of hemodynamic stability feature values; and displaying the label for each of the set of windows at a display.

14. The method of claim 13, wherein determining the set of consolidated ECG peaks comprises:

applying a set of multiple peak detection processes to the window to determine multiple sets of peaks;

comparing the multiple sets of peaks with each other and with a predetermined agreement threshold to determine an agreed set of peaks; and consolidating the agreed set of peaks to determine the set of consolidated ECG peaks.

15. The method of claim 14, wherein the set of multiple peak detection processes comprises a wavelet transform.

16. The method of claim 15, wherein the set of multiple peak detection processes comprises three peak detection processes, and wherein the predetermined agreement threshold requires an agreement between at least two peak detection processes.

17. The method of claim 13, further comprising checking the window for a first and second set of data criteria, wherein:

when any of the first set of data criteria are satisfied, the label for the window indicates that data is missing from the window; and when any of the second set of data criteria are satisfied, the label for the window indicates that the window is noisy.

18. The method of claim 17, wherein checking the window for a first and second set of data criteria is performed before determining the set of hemodynamic stability feature values, wherein the set of hemodynamic stability feature values is not determined when any of the first or second set of data criteria are met.

19. The method of claim 18, wherein displaying the label comprises displaying a time series bar chart comprising a set of bars, wherein each of the set of bars corresponds to a window and the label assigned to the corresponding window.

20. The method of claim 18, wherein displaying the label comprises displaying the label at a central nursing station of a healthcare facility associated with the patient.

* * * * *